US008672862B2

(12) United States Patent
Kanekasu (10) Patent No.: US 8,672,862 B2
(45) Date of Patent: Mar. 18, 2014

(54) APPARATUS FOR IDENTIFYING FEMORAL HEAD CENTER (76) Inventor: Koichi Kanekasu, Takaoka (JP)

(*) Notice: Subject to any disclaimer, the term of this patent is extended or adjusted under 35 U.S.C. 154(b) by 376 days.

(21) Appl. No.: 13/101,745

(22) Filed: May 5, 2011

(65) Prior Publication Data
US 2012/0029581 A1 Feb. 2, 2012

(30) Foreign Application Priority Data

Jul. 29, 2010 (JP) ................. 2010-170407

(51) Int. Cl.
A61B 5/103 (2006.01)
A61B 5/117 (2006.01)
A61F 2/46 (2006.01)

(52) U.S. Cl.
USPC ........................................ 600/587; 606/86 R (58) Field of Classification Search
USPC ............. 606/53, 60, 62–68, 86 R, 87–89, 91, 606/96–98, 102, 104, 105, 130; 33/511–512; 600/587, 588, 595; 602/32, 33, 35–37, 40
See application file for complete search history.

(56) References Cited

U.S. PATENT DOCUMENTS

| 5,007,912 A * | 4/1991 | Albrektsson et al. ........... 606/87 |
| 5,606,590 A * | 2/1997 | Petersen et al. ................ 378/177 |
| 5,616,147 A * | 4/1997 | Gadelius ........................ 606/102 |
| 5,690,638 A * | 11/1997 | Dance et al. .................... 606/88 |
| 6,383,149 B1 * | 5/2002 | DeMayo .......................... 600/587 |
| 7,695,476 B2 * | 4/2010 | Nevelos et al. ................. 606/87 |
| 7,805,852 B2 * | 10/2010 | Collette .......................... 33/511 |
| 2002/0010474 A1 * | 1/2002 | Chan .............................. 606/102 |
| 2003/0078520 A1 * | 4/2003 | DeMayo ........................ 600/587 |
| 2004/0210233 A1 * | 10/2004 | Yoon et al. ..................... 606/102 |
| 2008/0214960 A1 * | 9/2008 | Hodgson et al. .............. 600/587 |
| 2009/0076507 A1 | 3/2009 | Claypool et al. |
| 2010/0298834 A1 * | 11/2010 | Hildebrandt ................... 606/80 |
| 2012/0165706 A1 * | 6/2012 | Lavallee ........................ 600/595 |

FOREIGN PATENT DOCUMENTS

| JP | 2008515601 | 5/2008 |
| WO | WO-2006044367 | 4/2006 |
| WO | WO-2008/059211 A1 | 5/2008 |

OTHER PUBLICATIONS

Extended European Search Report for EP 11164428.2-1269, dated Nov. 23, 2011.

* cited by examiner

Primary Examiner — Matthew Lawson
(74) Attorney, Agent, or Firm — Marshall, Gerstein & Borun LLP (57) ABSTRACT An apparatus for identifying, during total knee replacement surgery, a position of a center of a femoral head of a patient within a plane parallel to a frontal plane, comprises a marking plate placed to cover, in a direction perpendicular to the frontal plane, a site where the femoral head center of the patient's body is located; a pivotal arm having a pivotal shaft arranged to extend in a direction perpendicular to the frontal plane; and a marker attached to the pivotal arm, for depicting a circular arc on the marking plate according to rotation of the pivotal arm; the pivotal shaft being placed at a distal end of a femur of the patient, a distance from the pivotal shaft to the marker in a direction parallel to the frontal plane being equal to a preliminarily measured distance from the distal end of the femur to the femoral head center.

9 Claims, 12 Drawing Sheets

APPARATUS FOR IDENTIFYING FEMORAL HEAD CENTER

BACKGROUND OF THE INVENTION

1. Field of the Invention

The invention relates to a femoral head center identifying apparatus for identifying the position of a femoral head center within a plane parallel to a frontal plane during total knee replacement surgery.

2. Description of Related Art

Generally speaking, when viewing an X-ray image (frontal plane image) of the anterior surface of a lower extremity, the weight bearing line of the human body conceivably passes through the central region of the knee joint, if the angle of intersection between the functional axis of the anterior surface of the femur which axis connects the femoral head center to the knee joint center, and the functional axis of the anterior surface of the os cruris which axis connects the knee joint center to the talus center (this angle is hereinafter referred to as "lower extremity alignment angle") is zero degree. Therefore, such a lower extremity alignment is regarded as an ideal alignment.

For the above reason, the goal of total knee replacement that involves replacement of at least a part of a knee joint with a joint prosthesis is to make the lower extremity alignment angle after surgery closest to zero degree, and there have been heretofore developed various surgical techniques and instruments intended to obtain angles within a range of ±3 degrees which are recognized as "optimum angles". One such example is the navigation system disclosed in JP-T-2008-515601 that is a computer-aided system for performing accurate total knee replacement. Use of this navigation system enables accurate identification of the position of a femoral head center during surgery with the aid of a computer, which makes it possible to install a block for bone resection in place in the femur while checking the position of the femoral head center so that accurate bone resection can be performed on the distal end of the femur. It is accordingly possible to place a joint prosthesis at the distal end of the femur that has been resected and, in consequence, excellent lower extremity alignment can be established with a post-surgery lower extremity alignment angle falling with the range of ±3 degrees.

This navigation system however has a problem that it incurs enormous development costs, resulting in a considerable increase in surgical expense. In addition, navigation marks (benchmarks) for use in identification of the position of the femoral head center need to be fixed to the femur, using pins which may cause damage to the femur.

To solve the above problems, there has been recently developed an inexpensive surgical technique called "shape matching" that uses no navigation systems. In this surgical technique, image data of the hip joint region and knee joint region are obtained by means of MRI or CT scan prior to surgery and a custom-made bone resection block for the patient is made based on the image data. During surgery, the bone resection block is mounted to the distal end of the femur and bone resection is performed without checking the position of the femoral head center. This shape matching technique does not require use of an expensive navigation system and can therefore save surgical expense. However, this technique has difficulty in achieving a high accuracy in bone resection, because the bone resection block is blindly mounted on the distal end of the femur without checking the position of the femoral head center. Therefore, it cannot be determined whether or not the bone resection block is in a correct position, based on the position of the femoral head center.

SUMMARY OF THE INVENTION

The invention is directed to overcoming the foregoing problems and therefore a primary object of the invention is to provide a femoral head center identifying apparatus capable of accurately identifying the position of a femoral head center even during surgery, with an inexpensive configuration.

According to the invention, there is provided a femoral head center identifying apparatus for identifying, during total knee replacement surgery, a position of a center of a femoral head of a patient undergoing the surgery within a plane parallel to a frontal plane, the apparatus comprising: a marking plate placed so as to cover, in a direction perpendicular to the frontal plane, a site where the femoral head center of the body of the patient is located; a pivotal arm having a pivotal shaft that is arranged so as to extend in a direction perpendicular to the frontal plane; and a marker attached to the pivotal arm, for depicting a circular arc on the marking plate according to rotation of the pivotal arm rotates, the pivotal shaft being placed at the distal end of a femur of the patient, a distance from the pivotal shaft to the marker in a direction parallel to the frontal plane being equal to a distance from the distal end of the femur to the femoral head center which distance has been measured preliminarily.

In this configuration, the distance from the pivotal shaft to the marker in a direction parallel to the frontal plane is equal to the distance from the distal end of the femur to the femoral head center which distance has been measured preliminarily, and the pivotal shaft is placed at the distal end of the femur. Therefore, when a circular arc is depicted on the marking plate with the marker by pivoting the pivotal arm, this circular arc passes through a point opposed to the femoral head center. Hence, when the hip joint is adducted or abducted thereby to position the femur in a first position and a second position which are distant from each other and a first circular arc and a second circular arc are depicted on the marking plate while the femur being located in these positions, the first and second circular arcs intersect each other at the point opposed to the femoral head center. With this intersection point, the position of the femoral head center can be identified within the plane parallel to the frontal plane. According to this configuration, the position of the femoral head center can be accurately identified within the plane parallel to the frontal plane, during total knee replacement surgery. In addition, since there is no need to employ a navigation system, surgery expense can be reduced and possible damage to the femur (e.g., damage caused by the pins used for securing the indicator section) can be avoided.

The pivotal arm may have a marker position adjusting mechanism for adjusting the distance from the pivotal shaft to the marker in a direction parallel to the frontal plane.

In this configuration, the distance from the pivotal shaft to the marker can be adjusted in accordance with the distance from the distal end of the femur to the femoral head center. This enables the femoral head center identifying apparatus to be equally applicable to a plurality of patients having different femur lengths.

The pivotal arm may have a tubular stem section secured to a deepest part of an intercondylar region at the distal end of the femur and an arm section pivotally inserted in the stem section.

Generally, the patients undergoing total knee replacement have damage in the medial and lateral condyles of the distal end of the femur and their medial and lateral condyles are distorted in shape depending upon the degree of damage. In contrast with this, the deepest part of the intercondylar region at the distal end of the femur is not affected by wear and bone destruction caused by load and is therefore unlikely to be deformed in shape. In this configuration, since the tubular stem section is secured at the deepest part of the intercondylar region at the distal end of the femur, stably secured state is attained.

The stem section may have at least two stem fastening pins to be inserted into the deepest part of the intercondylar region at the distal end of the femur.

In this configuration, the stem section is secured to the deepest part of the intercondylar region at the distal end of the femur by inserting the at least two stem fastening pings into the deepest part.

The pivotal arm may have a first rod and a second rod, and the marker position adjusting mechanism may have a reception section provided in the first rod, an insertion section provided in the second rod, and a fixing section for firmly fixing the first rod and the second rod to each other. The insertion section may be inserted into the reception section to a proper depth.

In this configuration, the distance from the pivotal shaft to the marker can be adjusted by adjusting the depth to which the insertion section is inserted into the reception section.

The pivotal arm may have a level indicator for detecting whether or not the pivotal shaft is perpendicular to the frontal plane.

In this configuration, since the pivotal arm can be pivoted while checking with the level indicator whether or not the pivotal shaft is perpendicular to the frontal plane, a circular arc depicted on the marking plate invariably passes through a position opposed to the femoral head center and therefore the position of the femoral head center can be accurately identified by depicting two circular arcs.

The femoral head center identifying apparatus may further comprise a surgical table for supporting the body of the patient so as to keep the frontal plane horizontal; and a plate supporting section attached to the surgical table, for detachably supporting the marking plate.

In this configuration, since the marking plate can be dismounted after identification of the position of the femoral head center, it is possible to prevent the marking plate from becoming an obstacle to the surgery.

The femoral head center identifying apparatus may further comprise an indicator section attached to the surgery table, for pointing out a point opposed to the femoral head center which point is marked in the marking plate with the marker.

In this configuration, the position of the femoral head center can be confirmed by the indicator section after detachment of the marking plate.

The total knee replacement surgery may include a step of securing a bone resection block to the distal end of the femur with a block fastening pin, and the pivotal arm may be integrally provided with a pin guide having a guide hole that serves as a guide used to insert the block fastening pin in the distal end of the femur.

In this configuration, the guide hole can be positioned in place with respect to the block fastening pin by positioning the marker such that it is opposed to the femoral head center. In consequence, the bone resection block can be accurately disposed in place by inserting the block fastening pin into a proper position of the distal end of the femur through the guide hole and securing the bone resection block with this block fastening pin.

The above and further objects and features of the invention will more fully be apparent from the following detailed description with reference to accompanying drawings.

DETAILED DESCRIPTION OF THE PREFERRED EMBODIMENTS

The outline of total knee replacement will be briefly described below and then the configurations and usages of the embodiments of the invention will be explained with reference to the accompanying drawings.

(General Outline of Total Knee Replacement)

Figure 1:
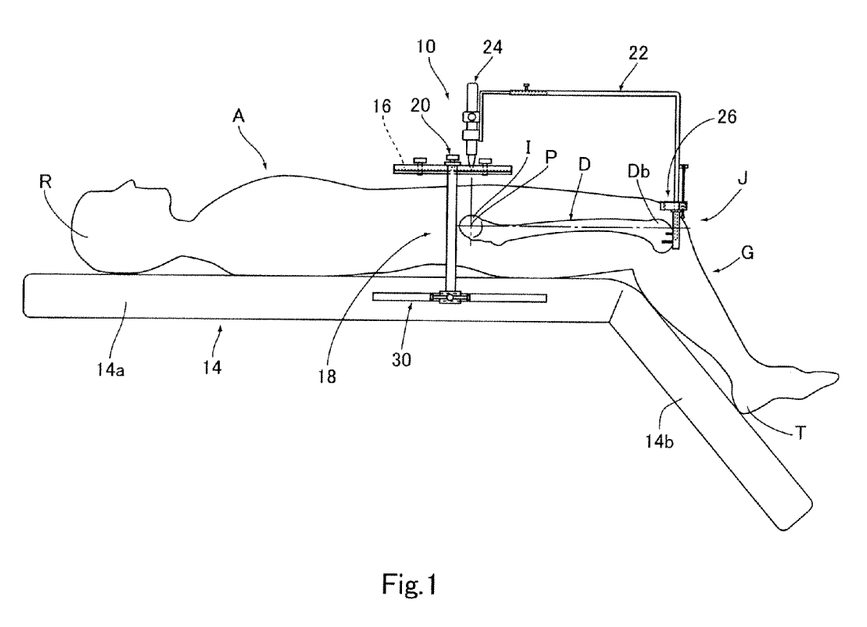
FIG. 1 is a front view showing a state where a femoral head center identifying apparatus according to a first embodiment of the invention is used in total knee replacement surgery.
Figure 2:
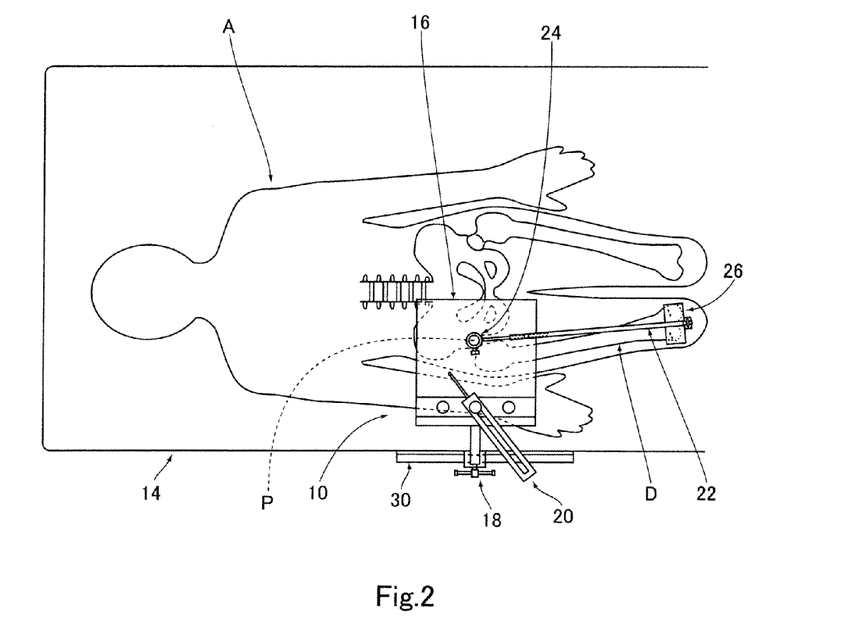
FIG. 2 is a plan view showing a state where the femoral head center identifying apparatus of the first embodiment is used in total knee replacement surgery.
Figure 3:
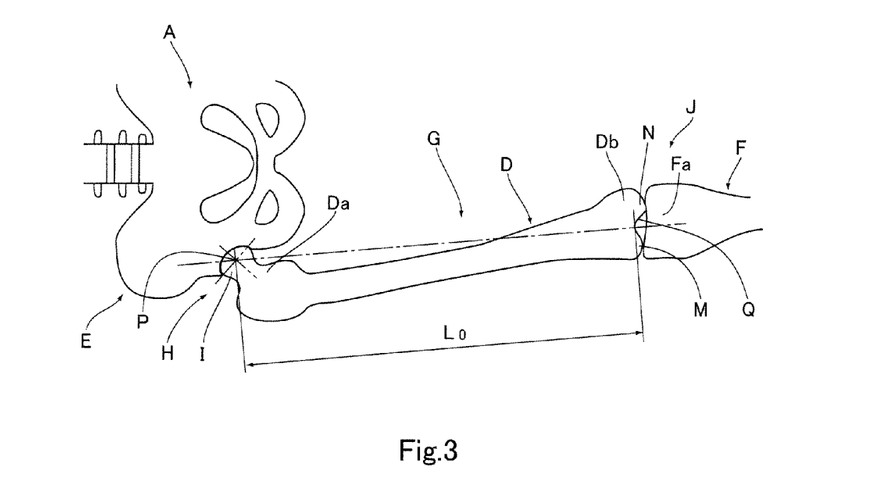
FIG. 3 is a view illustrating a structure of a femur and a tibia.
Figure 14:
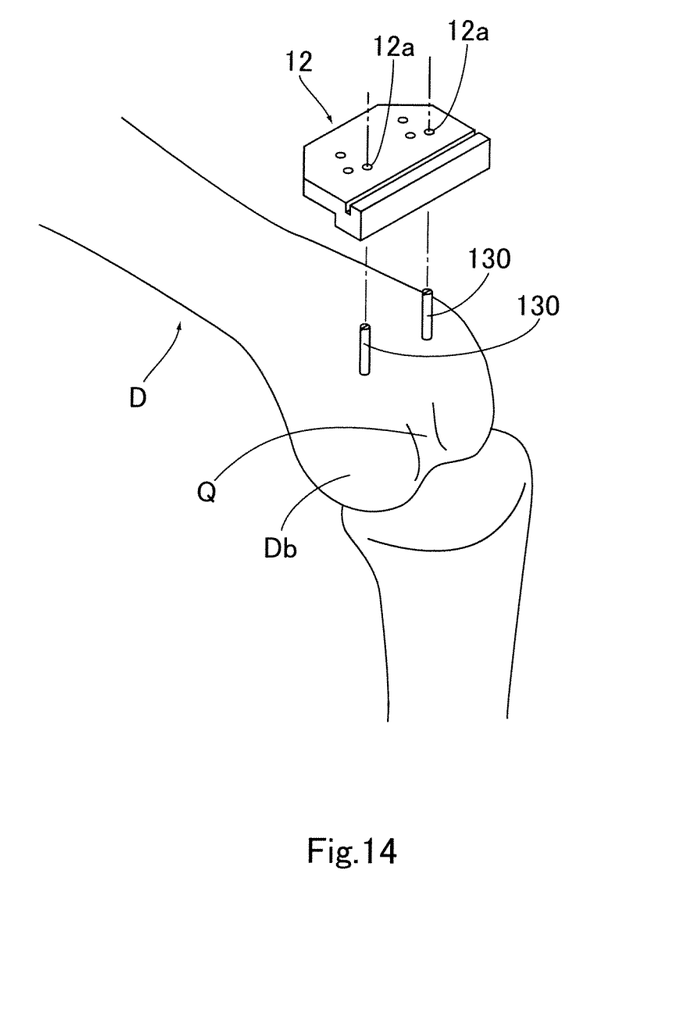
FIG. 14 is a perspective view illustrating the step of securing a bone resection block to the femur.
Figure 15:
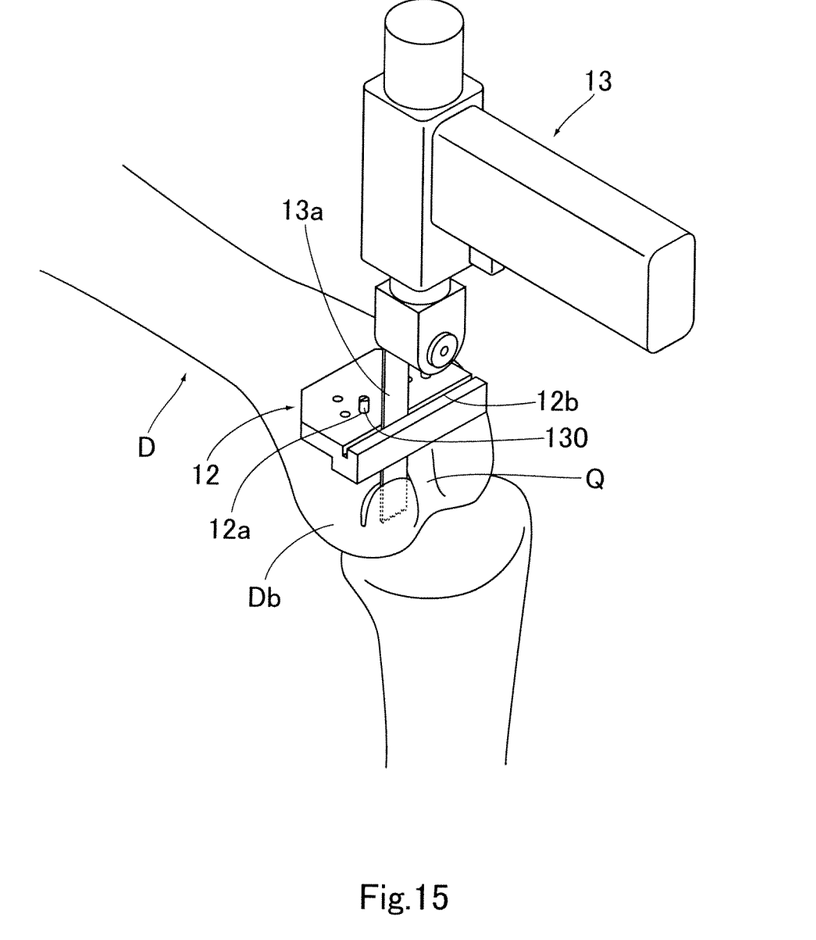
FIG. 15 is a perspective view illustrating the step of resecting the distal end of the femur.

FIG. 1 is a front view showing a physical state of a patient A undergoing the surgery of total knee replacement; FIG. 2 is a plan view showing the physical state of the patient A; and FIG. 3 illustrates the structure of a femur D and tibia F of the patient A. FIG. 14 is a perspective view showing the step of securing a bone resection block 12 to the femur D, whereas FIG. 15 is a perspective view showing the step of resecting the distal end Db of the femur during total knee replacement surgery.

As illustrated in FIG. 3, the femur D is a bone that is located between a pelvis E and the tibia F, constituting an extremity G. Situated at the proximal end Da of the femur is a femoral head I which constitutes a hip joint H. Situated at the femur distal end Db are a medial condyle M and a lateral condyle N which constitute a knee joint J. An intercondylar region Q, which is concave in shape, is located between the medial condyle M and the lateral condyle N. The medial condyle M and the lateral condyle N are in contact with a tibia proximal end Fa with cartilage interposed therebetween.

Total knee replacement is surgery for cutting the femur distal end Db and the tibia proximal end Fa out which became deformed owing to knee osteoarthritis, rheumatoid arthritis or the like and replacing the cut portion with a joint prosthesis (not shown in the drawing). A femoral head center identifying apparatus 10 is used for identifying the position of the center P of the femoral head I (i.e., femoral head center) in a plane parallel to the frontal plane during total knee replacement surgery. In a bone resection step, a bone resection block 12 is securely placed at a proper position based on the identified femoral head center P (FIG. 3) as shown in FIG. 14 and bone resection is performed by use of the bone resection block 12 and a bone saw 13 as shown in FIG. 15.

First Embodiment

Figure 4:
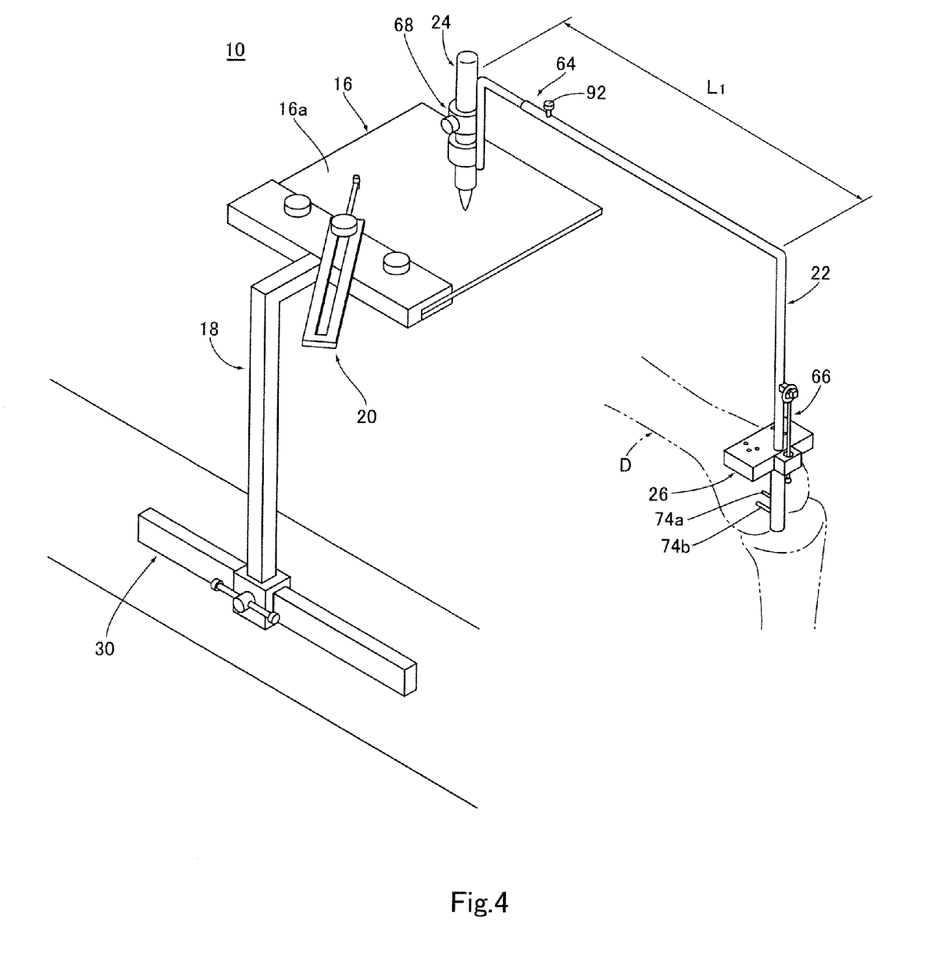
FIG. 4 is a perspective view illustrating a whole configuration of the femoral head center identifying apparatus of the first embodiment.

FIGS. 1 and 2 are a front view and plan view, respectively, showing a state where the femoral head center identifying apparatus 10 of the first embodiment is used in total knee replacement surgery. FIG. 4 is a perspective view showing the whole configuration of the femoral head center identifying apparatus 10.

As illustrated in FIGS. 1, 2 and 4, the femoral head center identifying apparatus 10 has a surgical table 14; a marking plate 16, a plate supporting section 18 and an indicator section 20 which are directly or indirectly attached to the surgical table 14; and a pivotal arm 22, a marker 24 and a pin guide 26 which are directly or indirectly attached to the femur D of the patient A.

Structure of Surgical Table

As illustrated in FIGS. 1 and 2, the surgical table 14 is for supporting the body of the patient A such that the frontal plane becomes horizontal and includes a first table 14a for supporting a region that extends from a knee joint J to a head R and a second table 14b for supporting a region that extends from the knee joint J to a heel T. At a connection part between the first table 14a and the second table 14b, a manually-operated or electrically-operated angle adjustment mechanism (not shown) for properly adjusting the angle of the second table 14b relative to the first table 14a. Horizontally attached to one side face of the first table 14a in a width direction is a rail 30 that supports the marking plate 16, the plate supporting section 18 and the indicator section 20 such that the marking plate 16, the plate supporting section 18 and the indicator section 20 are movable.

Structure of Marking Plate and Others

Figure 5:
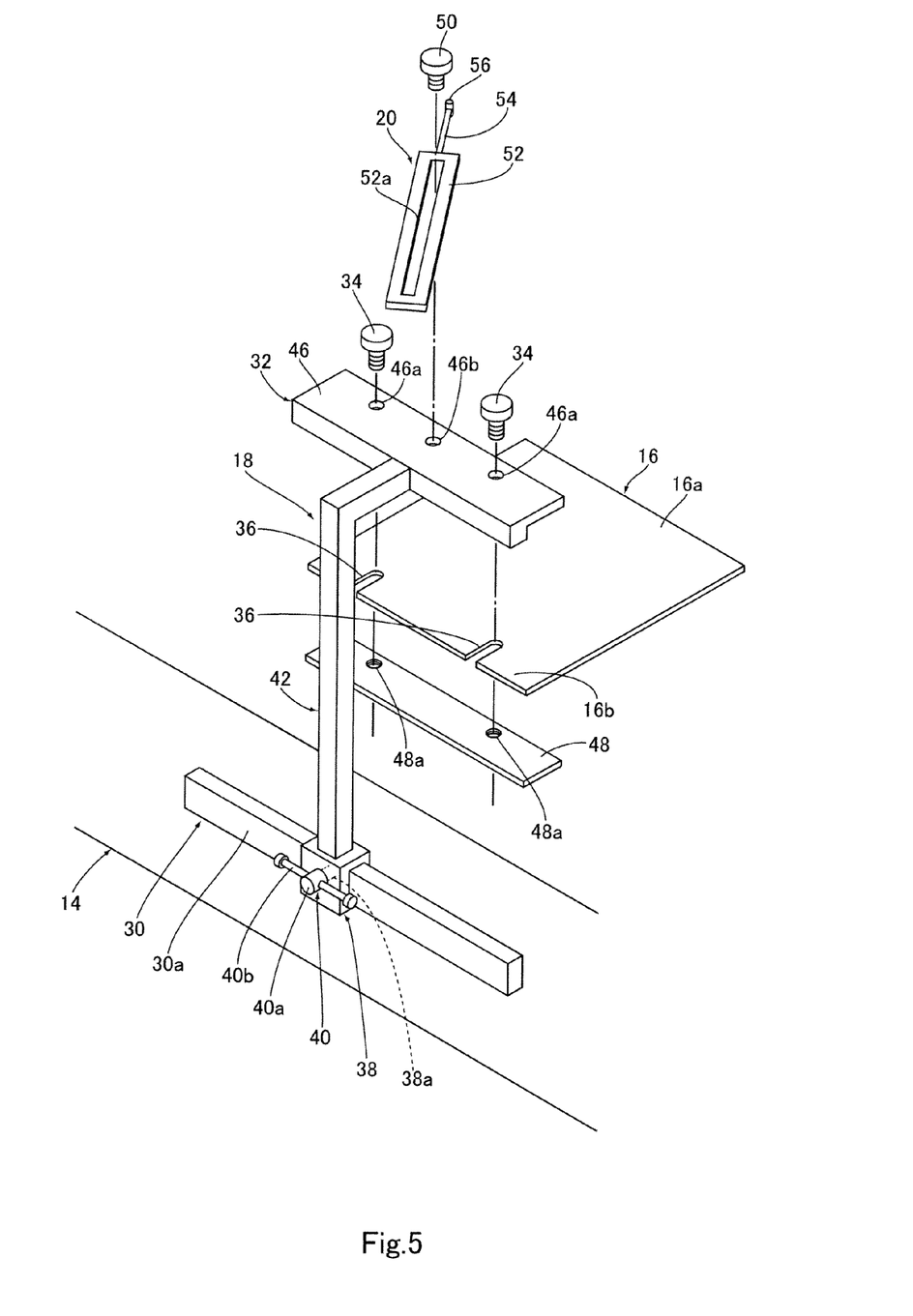
FIG. 5 is an exploded perspective view illustrating a configuration of a marking plate, a plate supporting section and an indicator section.

FIG. 5 is an exploded perspective view showing a configuration of the marking plate 16, the plate supporting section 18 and the indicator section 20.

As illustrated in FIGS. 1 and 2, the marking plate 16 is a plate-like member that is arranged so as to cover, in a direction perpendicular to the frontal plane, the site where the femoral head center P of the body of the patient A is located. In this embodiment, the marking plate 16 is made of a transparent acrylic material and has a rectangular shape (200 mm×200 mm). As shown in FIG. 5, a top surface 16a of the marking plate 16 is a smooth flat surface so that two circular arcs S1, S2 (FIG. 9) can be depicted thereon with the marker 24 (FIG. 4). This top surface 16a is oriented parallel to the frontal plane (the top surface 16a is horizontally arranged in this embodiment). A part of the peripheral portion of the marking plate 16 is a gripped section 16b gripped by a gripping section 32 of the plate supporting section 18. Formed in the gripped section 16b are two cutouts 36 through which fastening screws 34 are inserted.

Although the marking plate 16 is not limited to any particular material nor shape, the plate 16 is preferably made of a transparent material in view of its good visibility when checking the anatomical indications (such as anterior superior iliac spine, femoral artery and inguinal ligament) located under the marking plate 16 and preferably made of a resinous material in view of its good processability. In addition, the marking plate 16 preferably has a shape having a linear side (peripheral end) such as a rectangular shape or semi-circular shape because the marking plate 16 of such a shape can be securely gripped by the gripping section 32.

As illustrated in FIG. 5, the plate supporting section 18 is attached to the surgical table 14 via the rail 30, for detachably supporting the marking plate 16 and includes a sliding section 38, a stopper 40, a supporting column 42 and the gripping section 32.

The sliding section 38 is a member slidably fitted on the rail 30 and has a screw hole 38a that is defined in a portion of the sliding section 38 opposed to a side face 30a of the rail 30. The stopper 40 has a male screw 40a that is threadingly engageable into the screw hole 38a and a bar-like handle section 40b provided in the male screw 40a. In this configuration, when the male screw 40a is threaded into the screw hole 38a by rotating the handle section 40b, the tip end of the male screw 40a is pressed against the side face 30a of the rail 30 so that sliding of the sliding section 38 relative to the rail 30 is inhibited. When the handle section 40b is reversely rotated, the tip end of the male screw 40a is separated from the side face 30a of the rail 30, thereby allowing sliding of the sliding section 38 relative to the rail 30.

The supporting column 42 is a bar-like member for supporting the gripping section 32 at a specified height. The lower end of the supporting column 42 is connected to the sliding section 38 whereas the upper end thereof being connected to the gripping section 32. The gripping section 32 includes a base 46 secured to the upper end of the supporting column 42, a gripping strip 48 located under the base 46, and two fastening screws 34. The base 46 is provided with two through holes 46a through which the fastening screws 34 are inserted, and the gripping strip 48 is provided with two screw holes 48a into which the fastening screws 34 are threaded. Further, the base 46 is provided with a screw hole 46b into which a fastening screw 50 of the indicator section 20 is threaded.

The base 46 and the gripping strip 48 are joined together by means of the fastening screws 34, and the marking plate 16 is retained between the base 46 and the gripping strip 48 with the fastening screws 34 being inserted into the two cutouts 36 of the marking plate 16. According to this configuration, when dismounting the marking plate 16 from the gripping section 32, the marking plate 16 can be pulled out in a horizontal direction after slightly loosening the fastening screws 34.

As illustrated in FIG. 5, the indicator section 20 includes a position adjusting plate 52 attached to the surgical table 14 via the plate supporting section 18 and the rail 30; a supporting bar 54 provided at the tip end of the position adjusting plate 52; a pointer 56 provided at the tip end of the supporting bar 54; and a fastening screw 50. The position adjusting plate 52 has an elongated hole 52a through which the fastening screw 50 is inserted. The fastening screw 50 inserted in the elongated hole 52a is threaded into the screw hole 46b, thereby securing the indicator section 20 to the base 46. By loosening the fastening screw 50, a length of a protruding portion of the position adjusting plate 52 relative to the base 46 and an angle of the position adjusting plate 52 relative to the base 46, can be adjusted and the position of the pointer 56 with respect to the marking plate 16 can be adjusted.

Configuration of Pivotal Arm and Others

Figure 6:
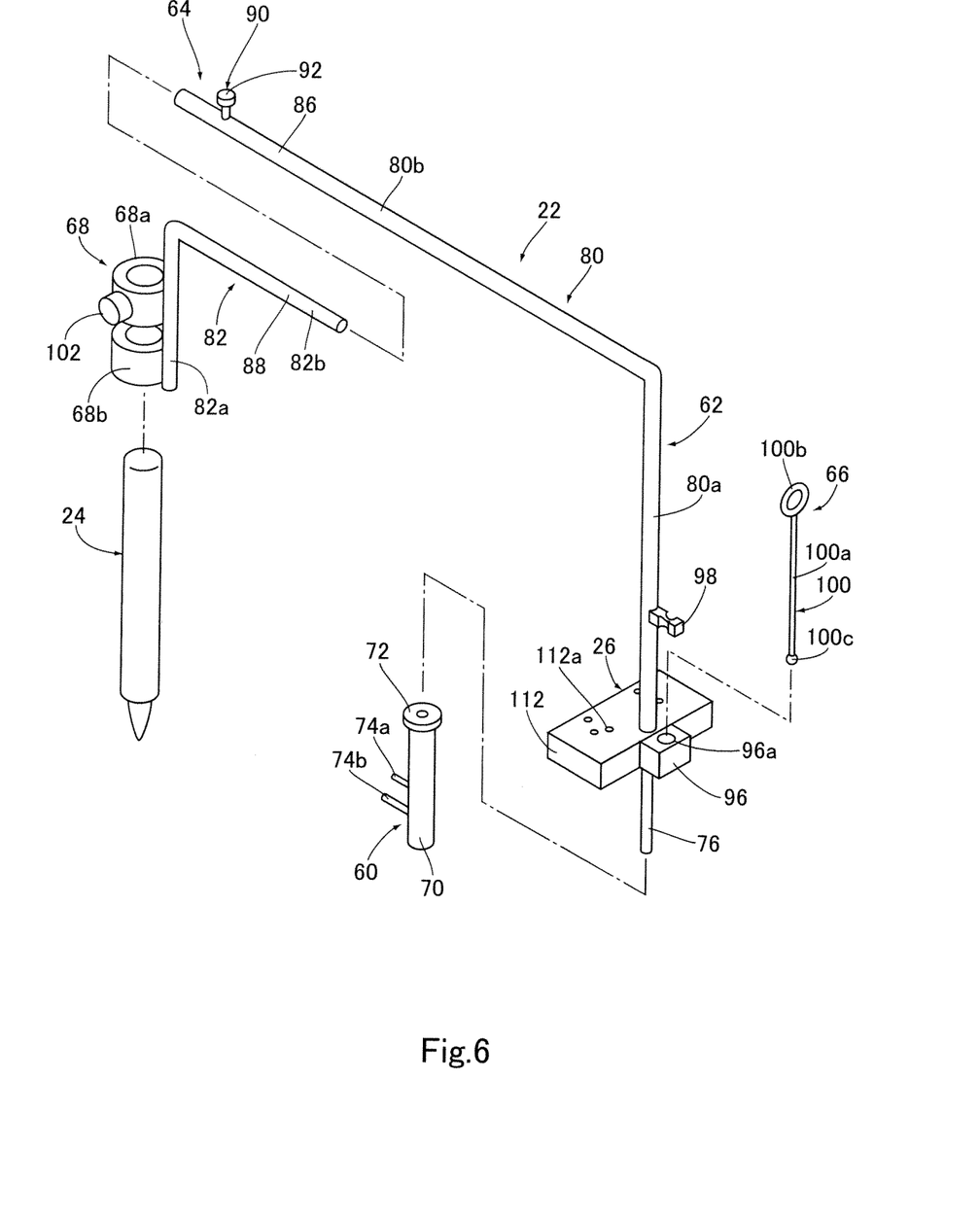
FIG. 6 is an exploded perspective view illustrating a configuration of a pivotal arm, a maker and a pin guide.

FIG. 6 is an exploded perspective view showing the pivotal arm 22, the marker 24 and the pin guide 26.

As seen from FIGS. 1 and 2, the pivotal arm 22 is a member directly attached to the femur D of the patient A and includes, as shown in FIG. 6, a tubular stem section 60 that is secured to the deepest part of the intercondylar region Q (FIGS. 7A, 7B) located in the femur distal end Db; an arm section 62 inserted in and pivotally supported by the stem section 60; a marker position adjusting mechanism 64; a level indicator 66 provided at the base end of the arm section 62; and a marker holder 68 provided at the tip end of the arm section 62.

As illustrated in FIG. 6, the stem section 60 has a tubular stem body 70, a flange portion 72 provided at the upper end of the stem body 70; and two stem fastening pins 74a, 74b provided in the side surface of the stem body 70, being spaced from each other in an axial direction.

The stem body 70 is placed at the deepest part of the intercondylar region Q (FIGS. 7A, 7B) located in the femur distal end Db so as to extend in a direction parallel to the anterior-posterior axis of the femur (that is a direction perpendicular to the frontal plane, and the same is applicable in the following description). The outer diameter of the stem body 70 is designed to be sufficiently smaller than the depth of a concave space of the intercondylar region Q so that the stem body 70 is accommodated in the concave space. The inner diameter of the stem body 70 is designed to be slightly larger than the outer diameter of a pivotal shaft 76 located at the base end of the arm section 62 so that the stem body 70 can pivotally support the pivotal shaft 76.

The flange portion 72 is a portion for determining the insertion length of the pivotal shaft 76 inserted in the stem body 70, and in this embodiment, the insertion length of the pivotal shaft 76 inserted in the stem body 70 is limited by a part of the lower surface of the pin guide 26 coming into contact with the upper surface of the flange portion 72. The stem fastening pins 74a, 74b are bar-like portions that are inserted in the deepest part of the intercondylar region Q (FIGS. 7A, 7B) in order to secure the stem section 60 to the femur distal end Db. The length of the stem fastening pin 74a located at an upper position is designed to be shorter than that of the stem fastening pin 74b located at a lower position. This allows the stem section 60 to incline to a certain degree within the sagittal plane and enables control of the angle of inclination of the stem section 60.

The arm section 62 includes a substantially L-shaped first rod 80 located on the base end side thereof; a substantially L-shaped second rod 82 located on the tip end side thereof; and the pivotal shaft 76 formed so as to extend continuously from the first rod 80.

The first rod 80 has a vertical portion 80a extending parallel to the anterior-posterior axis of the femur and a horizontal portion 80b extending horizontally from the upper end of the vertical portion 80a, the lower end of the vertical portion 80a being connected to the upper end of the pivotal shaft 76. The pin guide 26 is formed integrally with the arm section 62 in the connection part between the vertical portion 80a and the pivotal shaft 76 or in the vicinity thereof. The level indicator 66 is formed integrally with the arm section 62 in the above connection part or in the vicinity thereof, in a location above the pin guide 26. The second rod 82 has a vertical portion 82a extending parallel to the anterior-posterior axis of the femur and a horizontal portion 82b extending horizontally from the upper end of the vertical portion 82a, the vertical portion 82a being integrally provided with the marker holder 68. The first rod 80 and the second rod 82 are connected to each other via the marker position adjusting mechanism 64.

The marker position adjusting mechanism 64 includes a reception section 86 provided at the tip end of the horizontal portion 80b of the first rod 80; an insertion section 88 provided at the base end of the horizontal portion 82b of the second rod 82; and a fixing section 90 for firmly fixing the first rod 80 and the second rod 82 to each other. The insertion section 88 is inserted into the reception section 86 to a proper depth. The fixing section 90 includes a screw hole (not shown) defined in the reception section 86 and a fastening screw 92 threadingly engageable into this screw hole. By threading the fastening screw 92 into this screw hole, the tip of the fastening screw 92 is brought into contact with the insertion section 88, so that the reception section 86 and the insertion section 88 are secured to each other.

Figure 7A:
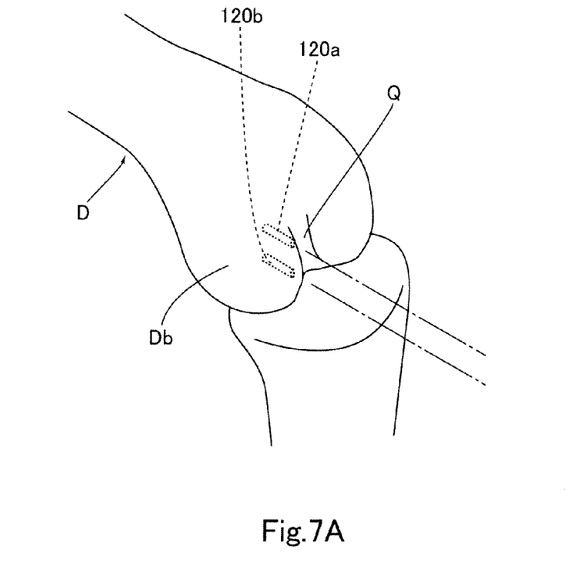
FIG. 7A is a perspective view illustrating a state in which holes are made in a deepest part of an intercondylar region, for receiving stem fastening pins inserted thereinto.
Figure 7B:
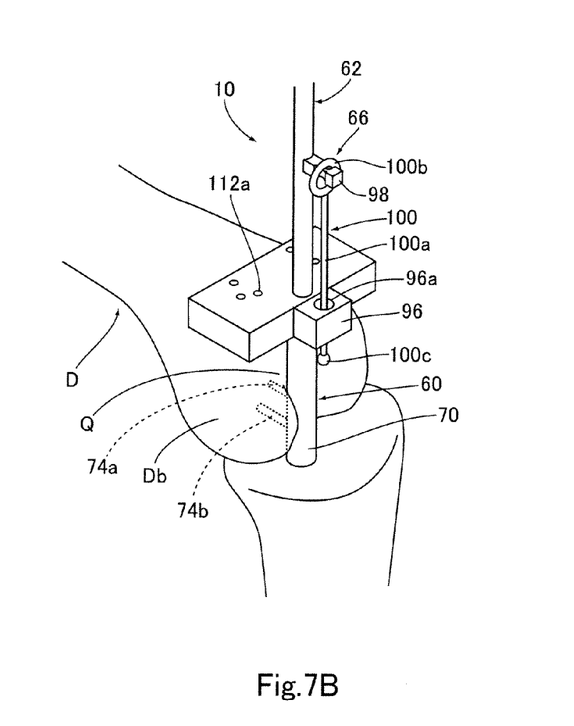
FIG. 7B is a perspective view illustrating a state where the stem fastening pins are inserted into the deepest part of the intercondylar region.

As illustrated in FIGS. 6 and 7B, the level indicator 66 includes a base 96 integrally mounted to the arm section 62; a mounting section 98 integrally attached to the arm section 62, in a location above the base 96; and a level indicator body 100 suspending from the mounting section 98. The level indicator body 100 has a bar-shaped shaft 100a, and an annular engagement portion 100b is formed at the upper end of the shaft 100a and is hooked by the mounting section 98. Formed at the lower end of the shaft 100a is a spherical weight 100c that pulls the shaft 100a down in the direction of gravitational force. Formed in the base 96 is a circular through hole 96a. The shaft 100a is inserted into the through hole 96a. The engagement portion 100b is hooked on the mounting section 98. In a state where the pivotal shaft 76 of the arm section 62 is oriented so as to extend in a vertical direction (i.e., direction perpendicular to the frontal plane), the shaft 100a is positioned at the center of the through hole 96a. Accordingly, the pivotal shaft 76 can be placed in a position perpendicular to the frontal plane by adjusting the inclination of the pivotal shaft 76 such that the shaft 100a is positioned at the center of the through hole 96a.

As illustrated in FIG. 6, the marker holder 68 has two annular retaining sections 68a, 68b which are attached to the vertical portion 82a of the second rod 82, being spaced from each other in a vertical direction. The inner diameter of the annular retaining sections 68a, 68b is designed to be slightly larger than the outer diameter of the marker 24. At least either one of the annular retaining sections 68a, 68b (the upper annular retaining section 68a in this embodiment) is provided with a screw hole (not shown) into which a fastening screw 102 is threadingly engageable. By threading the fastening screw 102 into this screw hole after insertion of the marker 24 into the annular retaining sections 68a, 68b, the tip of the fastening screw 102 is brought into contact with the marker 24 thereby to prevent the marker 24 from dropping off.

The marker 24 is for depicting circular arcs S1, S2 (FIG. 9) on the marking plate 16 and an ink pen is used as the marker 24 in this embodiment. It should be noted that the marker 24 is not limited to any particular type but may be a blade capable of inscribing the circular arcs S1, S2 on the marking plate 16.

Figure 11:
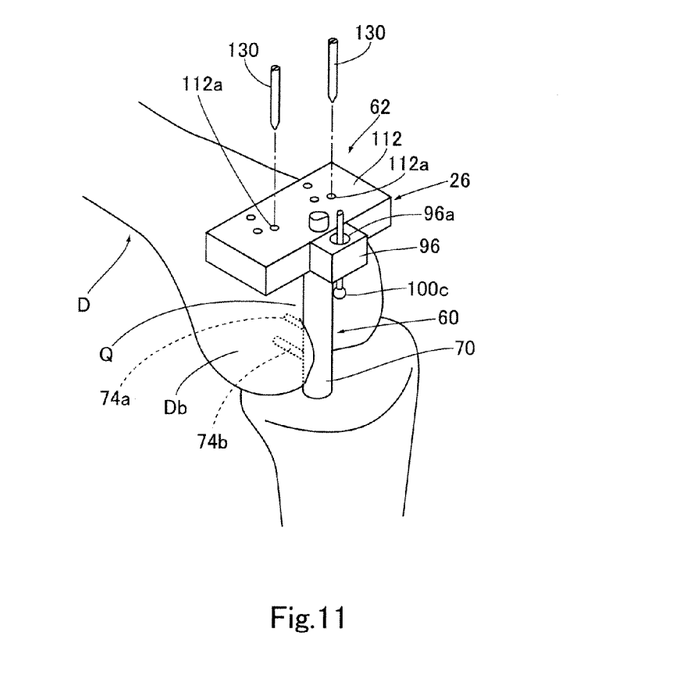
FIG. 11 is a perspective view illustrating the step of inserting block fastening pins into the femur through guide holes of the pin guide.

As shown in FIGS. 6 and 11, the pin guide 26 has a block-like guide body 112 formed integrally with the arm section 62, and the guide body 112 has a plurality of guide holes 112a respectively corresponding to a plurality of pin holes 12a (FIG. 14) provided in the bone resection block 12. The positions of the guide holes 112a in the pin guide 26 are determined in relation with the extending direction of the horizontal portions 80b, 82b of the arm section 62. Specifically, the horizontal portions 80b, 82b are designed to extend in a direction toward the femoral head center P when the specified guide holes 112a are positioned in place on the femur D. In addition, if the distance $L_1$ (FIG. 4) from the pivotal shaft 76 to the marker 24 in a direction parallel to the frontal plane is equal to the distance $L_0$ (FIG. 3) from the femur distal end Db to the femoral head center P which distance $L_0$ has been measured preliminarily, the marker 24 is located immediately above the femoral head center P.

Usage of Femoral Head Center Identifying Apparatus

Identification of Femoral Head Center

Figure 8:
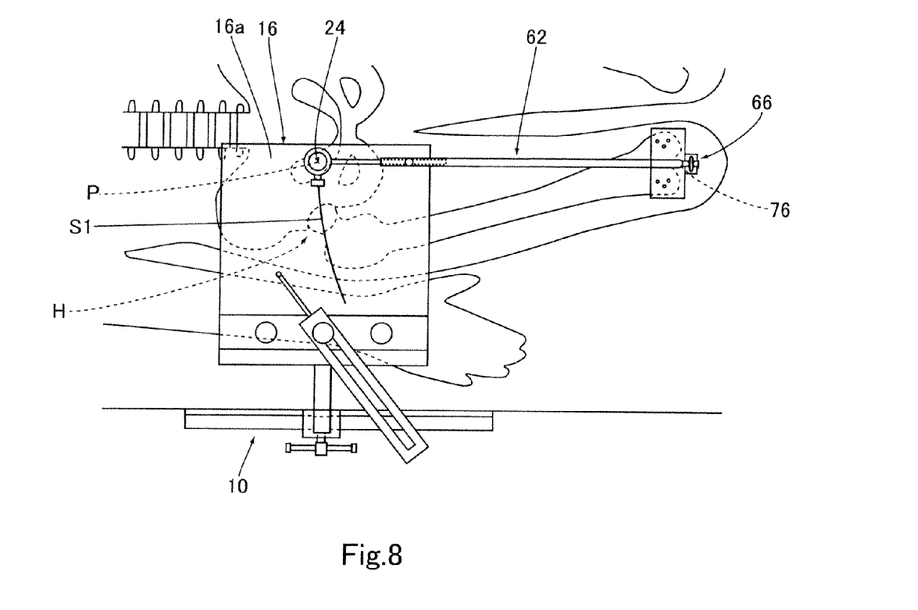
FIG. 8 is a plan view illustrating a state where a first circular arc is depicted in the marking plate.
Figure 9:
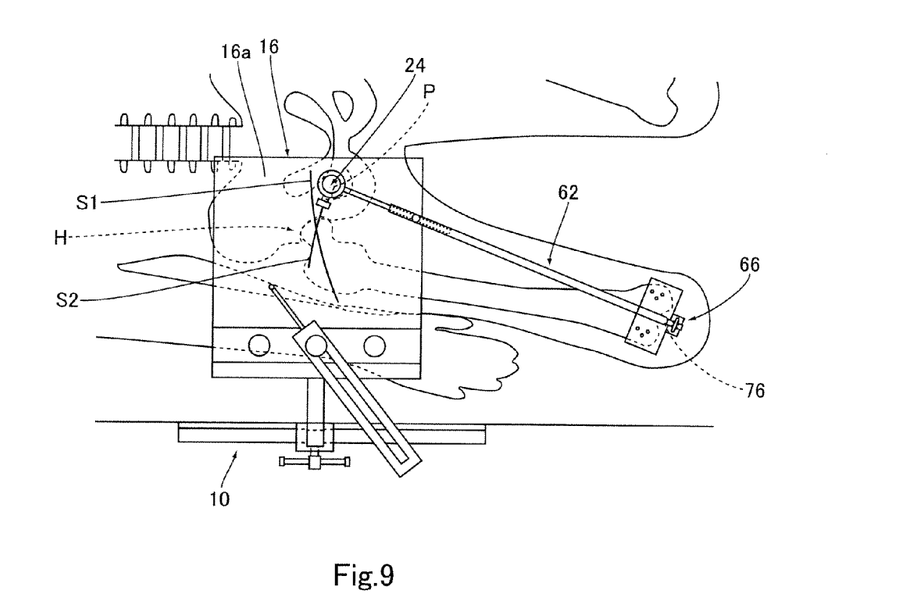
FIG. 9 is a plan view illustrating a state where a second circular arc is depicted in the marking plate.

FIG. 7A is a perspective view showing a state where holes 120a, 120b are made in the deepest part of the intercondylar region Q, for receiving the stem fastening pins 74a, 74b inserted therein, whereas FIG. 7B is a perspective view showing a state where the stem fastening pins 74a, 74b are inserted into the deepest part of the intercondylar region Q. FIG. 8 is a plan view showing a state where the first circular arc S1 is depicted on the marking plate 16, whereas FIG. 9 is a plan view showing a state where the second circular arc S2 is depicted on the marking plate 16.

Prior to total knee replacement surgery, the image of the femur D is taken as shown in FIG. 3, using X-ray imaging device. Then, the dimension of the picked-up image is corrected so as to be coincident with the actual dimension in accordance with the optical magnification of the X-ray imaging device, and the distance $L_0$ from the femur distal end Db to the femoral head center P is measured based on the corrected dimension. Subsequently, the distance $L_1$ from the pivotal shaft 76 to the marker 24 of the femoral head center identifying apparatus 10 is adjusted by the marker position adjusting mechanism 64 as shown in FIG. 4 such that the distance $L_1$ becomes equal to the distance $L_0$, and the fastening screw 92 is threaded thereby to prevent fluctuations in the distance $L_1$ ($=L_0$).

During total knee replacement surgery, the two holes 120a, 120b are so formed using a drill or the like as to be spaced in a vertical direction at the deepest part of the intercondylar region Q of the femur distal end Db as shown in FIG. 7A. Then, the stem fastening pins 74a, 74b of the stem section 60 are inserted into the holes 120a, 120b respectively as shown in FIG. 7B, and the pivotal shaft 76 of the arm section 62 is inserted into the stem body 70. As shown in FIG. 4, the marker 24 is mounted to the marker holder 68.

After the hip joint H is slightly adducted (about 5 degree adduction) from the neutral position of adduction/abduction, the arm section 62 is pivoted to allow the marker 24 to depict the first circular arc 51 on the top surface 16a of the marking plate 16, as shown in FIG. 8. At that time, the pivotal shaft 76 (FIG. 4) is kept upright with respect to the frontal plane while confirming it with the level indicator 66, whereby the first circular arc 51 is made to pass immediately above the femoral head center P without fail.

After completion of the depiction of the first circular arc 51, the hip joint H is slightly abducted (about 15 to 25 degree abduction) from the neutral position of adduction/abduction and then, the arm section 62 is pivoted to allow the marker 24 to depict the second circular arc S2 on the top surface 16a of the marking plate 16 as shown in FIG. 9. At that time, the pivotal shaft 76 (FIG. 4) is kept upright with respect to the frontal plane, whereby the second circular arc S2 is allowed to pass immediately above the femoral head center P without fail. Accordingly, the first circular arc 51 and the second circular arc S2 intersect at a point V immediately above the femoral head center P, and the femoral head center P can be identified within a plane parallel to the frontal plane, using this intersection point V as a guide mark.

Insertion of Block Fastening Pin

Figure 10:
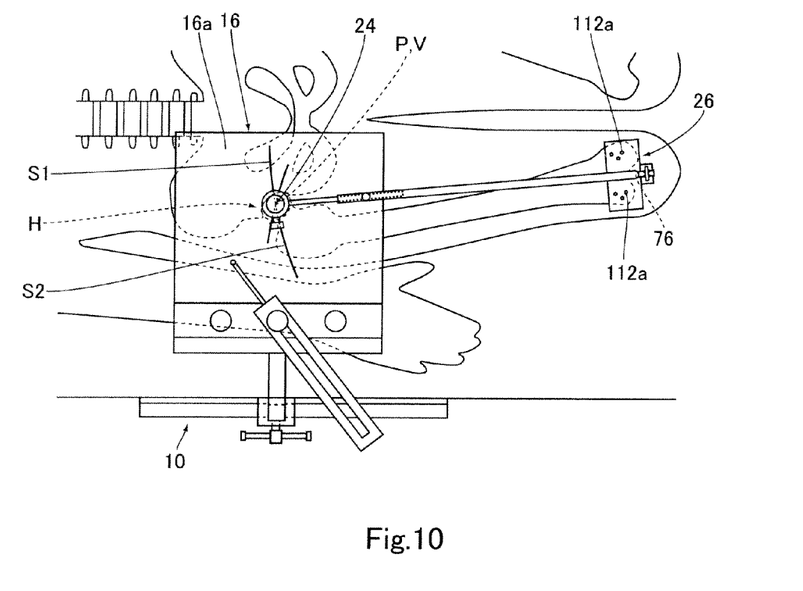
FIG. 10 is a plan view illustrating a state where the marker is placed in a position opposed to a femoral head center.
Figure 12:
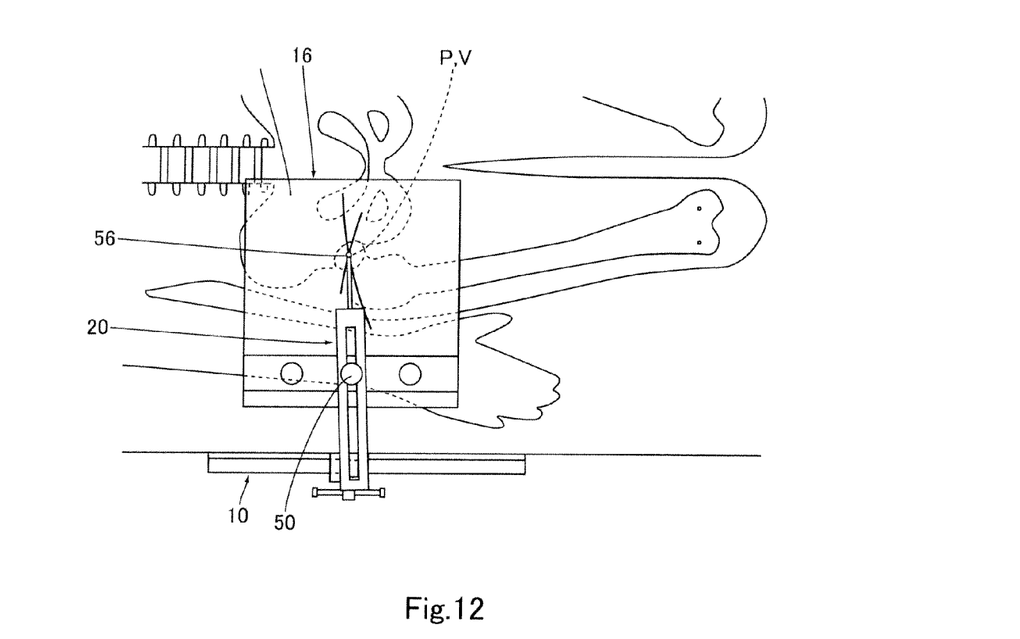
FIG. 12 is a plan view illustrating a state where the pivotal arm has been dismounted from the femoral head center identifying apparatus of the first embodiment.
Figure 13:
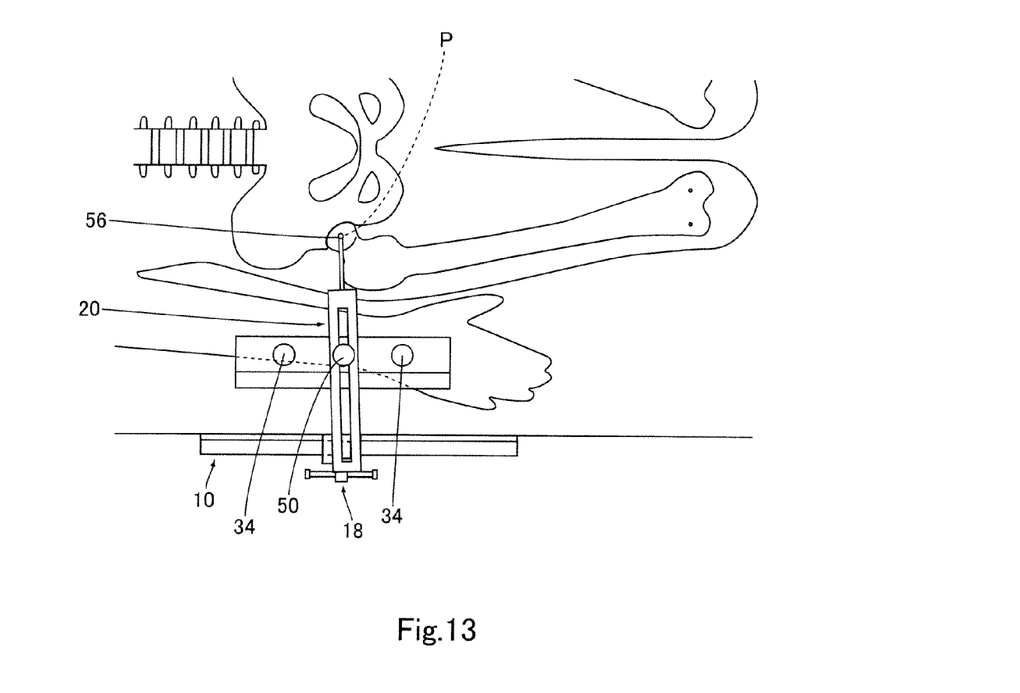
FIG. 13 is a plan view illustrating a state where the marking plate has been dismounted from the femoral head center identifying apparatus of the first embodiment and where the position opposed to the femoral head center is pointed out by the indicator section.

FIG. 10 is a plan view showing a state where the marker 24 is positioned to be opposed to the femoral head center P, whereas FIG. 11 is a perspective view showing the step of inserting block fastening pins 130 into the femur D through the guide holes 112a of the pin guide 26. FIG. 12 is a plan view showing a state where the pivotal arm 22 of the femoral head center identifying apparatus 10 is dismounted, whereas FIG. 13 is a plan view showing a state where the marking plate 16 of the femoral head center identifying apparatus 10 is dismounted and the position opposed to the femoral head center P is indicated by the indicator section 20.

After the position of the femoral head center P is identified by the intersection point V, the marker 24 is positioned at the intersection point V, thereby properly positioning the guide holes 112a of the pin guide 26 in alignment with the pin holes 12a of the bone resection block 12 (FIG. 14), as shown in FIG. 10. Specifically, the proper positions for the pin holes 12a are determined, using the femoral head center P as a benchmark.

Subsequently, as illustrated in FIG. 11, the block fastening pins 130 are made to pass through one of the three guide holes 112a located at the right side when viewed by the patient A and one of the three guide holes 112a located at the left side when viewed by the patient A, respectively. Then, the block fastening pins 130 are inserted into the femur D while being guided by these guide holes 112a. In FIG. 11, the arm section 62 and the level indicator 66 are cut away in the vicinity of the pin guide 26 for the sake of clearing illustrating the pin guide 26.

After completion of the insertion of the block fastening pins 130 into the femur D, the pivotal arm 22, the marker 24 and the pin guide 26 are dismounted and the pointer 56 of the indicator section 20 is positioned at the intersection point V, as illustrated in FIG. 12. Then, the fastening screws 34 of the plate supporting section 18 are loosened to dismount the marking plate 16, as shown in FIG. 13. Specifically, the marking plate 16, which could be an obstacle to the subsequent surgery, is removed, and confirmation of the position of the femoral head center P by the indicator section 20 smaller in size than the indicator section is made possible.

Bone Resection Step

FIG. 14 is a perspective view showing the step of securing the bone resection block 12 to the femur D, whereas FIG. 15 is a perspective view showing the step of resecting the femur distal end Db.

When resecting the femur distal end Db, the block fastening pins 130 inserted into the femur D are inserted into their corresponding pin holes 12a of the bone resection block 12 as shown in FIG. 14, whereby the bone resection block 12 is secured to a proper position of the femur D. Then, the blade 13a of the bone saw 13 is inserted into a slit 12b provided in the bone resection block 12 as shown in FIG. 15 and the femur distal end Db is resected along the slit 12b.

According to this embodiment, since the block fastening pins 130 can be inserted in place using the femoral head center P (FIG. 10) as a benchmark, the bone resection block 12 can be secured in place by means of the block fastening pins 130. Accordingly, accurate resection of the femur distal end Db becomes possible and a good lower extremity alignment can be achieved after mounting a joint prosthesis on the femur distal end Db.

Second Embodiment

Figure 16:
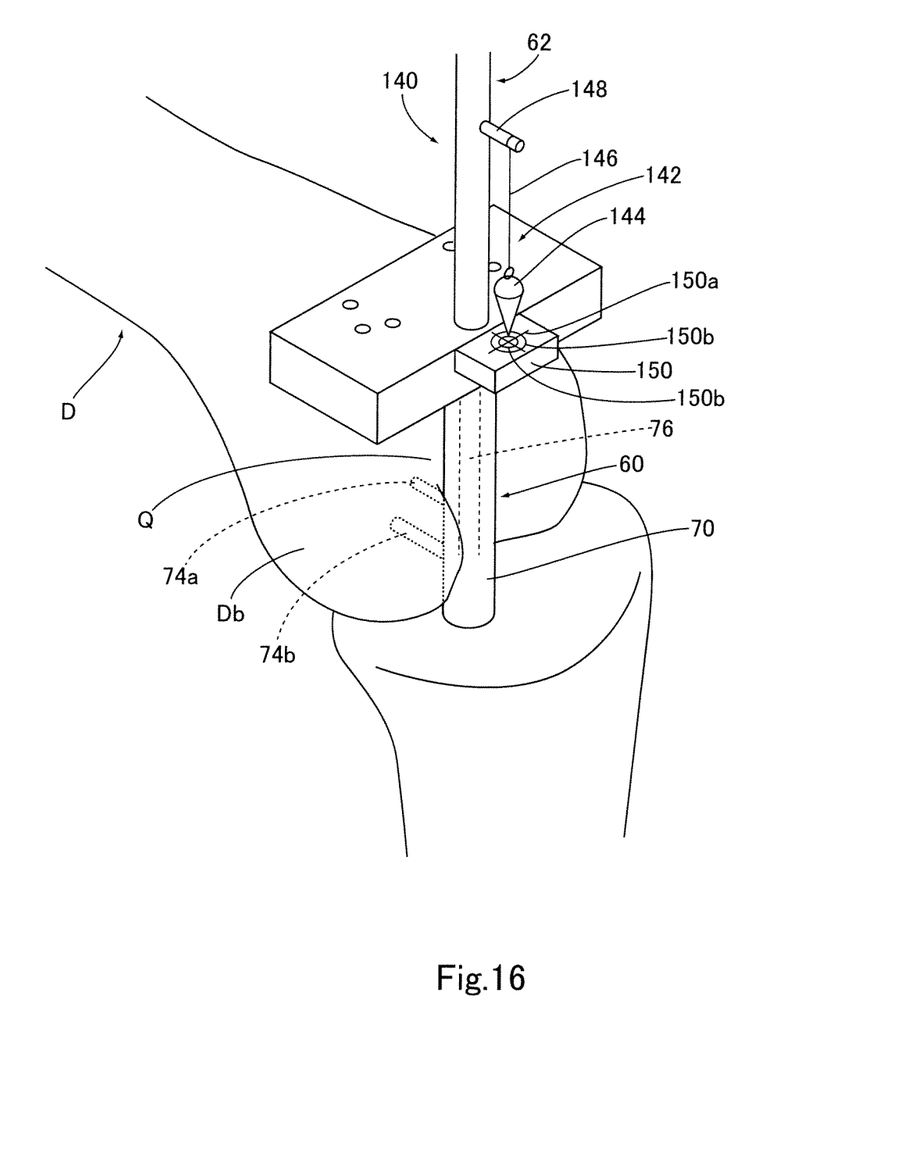
FIG. 16 is a perspective view illustrating the configuration of a level indicator provided in a femoral head center identifying apparatus according to a second embodiment.

FIG. 16 is a perspective view showing a configuration of a level indicator 142 provided in a femoral head center identifying apparatus 140 according to the second embodiment.

As shown in FIG. 16, in the femoral head center identifying apparatus 140 of the second embodiment, the level indicator 142 has a weight 144, a thread 146, a mounting section 148 and a plate 150, and the mounting section 148 and the plate 150 are integral with the arm section 62. In a position above the plate 150, the weight 144 is attached to the mounting section 148 through the thread 146 so as to suspend therefrom. A cross line 150a and a plurality of concentric circles 150b having different diameters are depicted on the top surface of the plate 150. When the pivotal shaft 76 is oriented in a vertical direction (i.e., a direction perpendicular to the frontal plane), the weight 144 is located in the center of the cross line 150a and the plurality of concentric circles 150b. Therefore, the direction of inclination of the pivotal shaft 76 can be obtained by checking the oriented direction of the weight 144 with respect to the cross line 150a, and the degree of inclination of the pivotal shaft 76 can be obtained by checking which of the plurality of concentric circles 150b the weight 144 is positioned at.

As this invention may be embodied in several forms without departing from the spirit of essential characteristics thereof, the present embodiments are therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A femoral head center identifying apparatus for identifying, during total knee replacement surgery, a position of a center of a femoral head of a patient undergoing the surgery within a plane parallel to a frontal plane, the apparatus comprising:
    a marking plate placed so as to cover, in a direction perpendicular to the frontal plane, a site where the femoral head center of a body of the patient is located;
    a pivotal arm having a pivotal shaft that is arranged so as to extend in a direction perpendicular to the frontal plane; and
    a marker attached to the pivotal arm, for depicting a circular arc on the marking plate according to rotation of the pivotal arm;
    the pivotal shaft is configured to be placed at a distal end of a femur of the patient,
    a distance from the pivotal shaft to the marker in a direction parallel to the frontal plane being equal to a measured preliminary distance from the distal end of the femur to the femoral head center.

2. The femoral head center identifying apparatus according to claim 1,
    wherein the pivotal arm has a marker position adjusting mechanism for adjusting the distance from the pivotal shaft to the marker in a direction parallel to the frontal plane.

3. The femoral head center identifying apparatus according to claim 2, wherein the pivotal arm has a first rod and a second rod,
    wherein the marker position adjusting mechanism has a reception section provided in the first rod, an insertion section provided in the second rod, and a fixing section for fixing the first rod and the second rod to each other, and
    wherein the insertion section is inserted into the reception section to a depth sufficient to permit the insertion section of the second rod to be securely received by the reception section of the first rod.

4. The femoral head center identifying apparatus according to claim 1,
    wherein the pivotal arm has a tubular stem section securable to a deepest part of an intercondylar region at the distal end of the femur and an arm section pivotally inserted in the stem section.

5. The femoral head center identifying apparatus according to claim 4,
    wherein the stem section has at least two stem fastening pins to be inserted into the deepest part of the intercondylar region at the distal end of the femur.

6. The femoral head center identifying apparatus according to claim 1,
    wherein the pivotal arm has a level indicator for detecting whether or not the pivotal shaft is perpendicular to the frontal plane.

7. The femoral head center identifying apparatus according to claim 1, further comprising:
    a surgical table for supporting the body of the patient so as to keep the frontal plane horizontal; and
    a plate supporting section attached to the surgical table, for detachably supporting the marking plate.

8. The femoral head center identifying apparatus according to claim 7, further comprising:
    an indicator section attached to the surgery table, the indicator section for pointing out a point opposed to the femoral head center which is marked in the marking plate with the marker.

9. The femoral head center identifying apparatus according to claim 1, wherein the total knee replacement surgery includes a step of securing a bone resection block to the distal end of the femur with a block fastening pin, and
    wherein the pivotal arm is integrally provided with a pin guide having a guide hole that serves as a guide used to insert the block fastening pin in the distal end of the femur.

* * * * *